US012799077B2

(12) United States Patent
Sengupta et al.

(10) Patent No.: US 12,799,077 B2
(45) Date of Patent: Nov. 17, 2026

(54) PROCESS FOR PREPARING DIPHENYLUREIDO-DIHALOKYNURENIC ACIDS AND TOSYLATE ADDITION SALTS THEREOF

(71) Applicant: LOHOCLA RESEARCH CORPORATION, Aurora, CO (US)

(72) Inventors: Ananya Sengupta, Schenectady, NY (US); Sergiy Krasutsky, Delmar, NY (US); Scott Tweedie, Albany, NY (US); Gurusankar Ramamoorthy, Guilderland, NY (US)

(73) Assignee: LOHOCLA RESEARCH CORPORATION, Aurora, CO (US)

( * ) Notice: Subject to any disclaimer, the term of this patent is extended or adjusted under 35 U.S.C. 154(b) by 0 days.

(21) Appl. No.: 19/635,254

(22) Filed: Mar. 31, 2026

(65) Prior Publication Data

US 2026/0217654 A1 Jul. 30, 2026

Related U.S. Application Data

(63) Continuation of application No. 19/355,488, filed on Oct. 10, 2025, now abandoned, which is a continuation-in-part of application No. 17/669,767, filed on Feb. 11, 2022, now Pat. No. 12,503,441, which is a continuation-in-part of application No. PCT/US2020/046038, filed on Aug. 12, 2020, which is a continuation of application No. 16/537,936, filed on Aug. 12, 2019, now Pat. No. 10,875,831.

(51) Int. Cl.
*C07D 215/46* (2006.01)
*A61K 31/4375* (2006.01)
*C07D 215/48* (2006.01)

(52) U.S. Cl.
CPC ........ *C07D 215/48* (2013.01); *A61K 31/4375* (2013.01); *C07D 215/46* (2013.01)

(58) Field of Classification Search
CPC .......................... C07D 215/46; A61K 31/4375
See application file for complete search history.

(56) References Cited

U.S. PATENT DOCUMENTS

| | | | | |
|---|---|---|---|---|
| 4,380,632 A | | 4/1983 | Steffen | |
| 6,962,930 B1 | | 11/2005 | Tabakoff | |
| 7,923,458 B2 | * | 4/2011 | Tabakoff | A61P 25/04 514/312 |
| 10,112,905 B2 | * | 10/2018 | Tabakoff | C07D 215/48 |
| 10,391,088 B2 | * | 8/2019 | Tabakoff | A61K 31/4706 |
| 10,435,371 B2 | * | 10/2019 | Tabakoff | C07D 215/48 |
| 11,130,737 B2 | * | 9/2021 | Tabakoff | C07D 215/48 |
| 2017/0204064 A1 | | 7/2017 | Tabakoff | |

OTHER PUBLICATIONS

Dorow et al., "Development of an Efficient Synthesis of the Pyrroloquinolone PHA- 529311," Organic Process Research and Development, 2006, vol. 10, pp. 493-499.
International Search Report and Written Opinion for Application No. PCT/US2020/046038, mailed Jan. 19, 2021, 8 pages.
Mugnaini et al. 'The 4-Quinolone-3-Carboxylic Acid Motif as a Multivalent Scaffold in Medicinal Chemistry', Current Med Chem., 2009, vol. 16, pp. 1746-1767.
Park et al., "A Facile Synthesis of 4-hydroxycoumarin and 4-hydroxy-2-quinolone Derivatives," Bull Korean Chem. Soc, 2007, vol. 28, No. 7, pp. 1203-1205.
Snell et al., "Novel structure having antagonist actions at both the glycine site of the N-methyl-D-aspartate receptor and neuronal voltage-sensitive sodium channels: biochemical, electrophysiological, and behavioral characterization," J Pharm & Exp Therapeutics, 2000, vol. 292, No. 1, pp. 215-227.

* cited by examiner

*Primary Examiner* — D Margaret M Seaman
(74) *Attorney, Agent, or Firm* — NORTON ROSE FULBRIGHT US LLP

(57) ABSTRACT

A crystalline compound having a formula of:

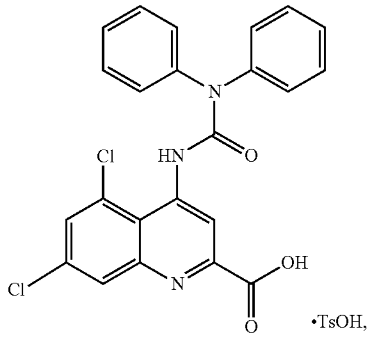

•TsOH, wherein the TsOH is p-toluenesulfonic acid is disclosed.

9 Claims, 1 Drawing Sheet

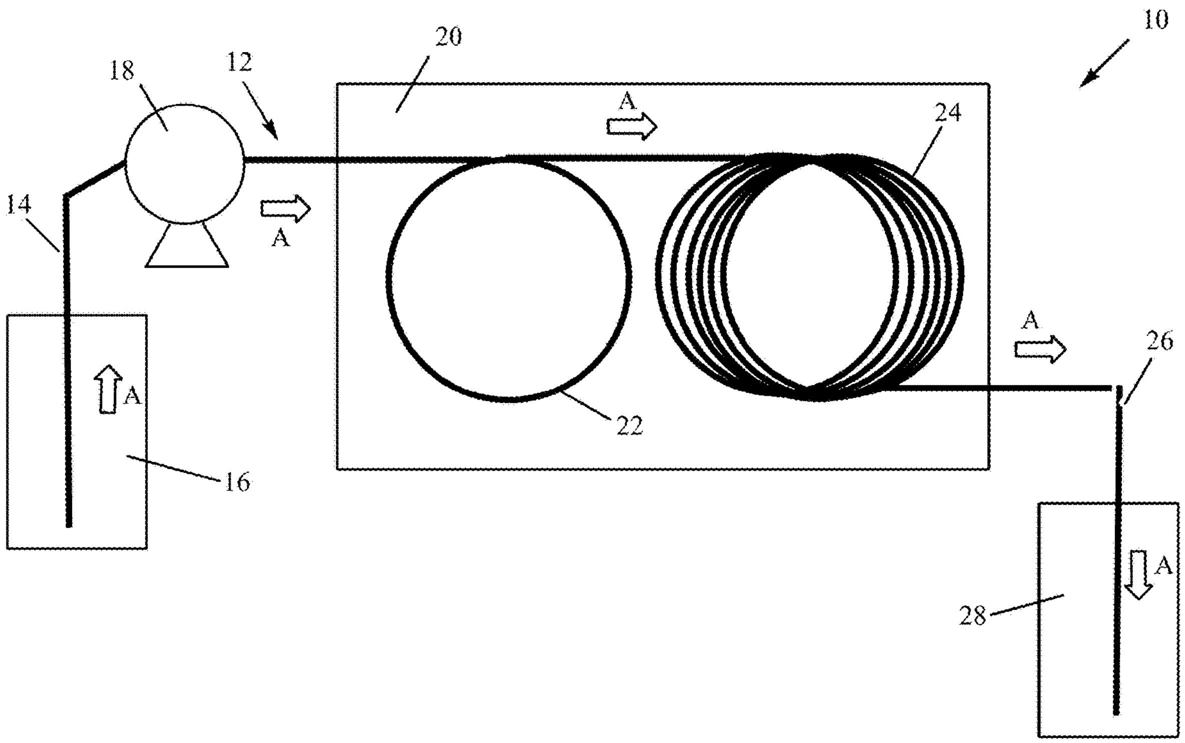
10
20
18
12
A
24
14
A
A
26
A
22
16
A
28

PROCESS FOR PREPARING DIPHENYLUREIDO-DIHALOKYNURENIC ACIDS AND TOSYLATE ADDITION SALTS THEREOF

CROSS-REFERENCE TO RELATED APPLICATIONS

This application is a continuation of U.S. application Ser. No. 19/355,488, filed Oct. 10, 2025, which is a continuation-in-part of U.S. application Ser. No. 17/669,767, filed Feb. 11, 2022 (issued as U.S. Pat. No. 12,503,441), which is a continuation-in-part of PCT/US2020/046038, filed Aug. 12, 2020, which is a continuation of U.S. application Ser. No. 16/537,936, filed Aug. 12, 2019 (issued as U.S. Pat. No. 10,875,831). Each of U.S. Ser. No. 17/669,767, PCT/US2020/046038, and U.S. Ser. No. 16/537,936 are incorporated by reference.

FIELD OF THE INVENTION

The present invention relates to process for preparing diphenylureido-dihalokynurenic acids, and tosylate addition salts thereof.

BACKGROUND OF THE INVENTION

4-Ureido-5,7-dihalo-quinoline-2-carboxylate compounds, particularly diphenylureido-dichlorokynurenic acid (DCUKA) compounds and esters thereof, reportedly have analgesic activity and are useful in treating chronic pain and alcohol dependence, as well as preventing relapse in alcohol addicted subjects. One difficulty in the commercial development of the 4-ureido-5,7-dihalo-quinoline-2-carboxylate compounds has been the harsh conditions needed for preparing 5,7-dihalo-1,4-dihydro-4-oxoquinoline-2-carboxylates, which are intermediates in the synthesis of the 4-ureido-5,7-dihalo-quinoline-2-carboxylate compounds. A published approach for preparing DCUKA ester compounds (e.g., the methyl or ethyl ester), is illustrated in Scheme 1 for the ethyl (Et) ester. Reaction A in Scheme 1 below comprises heating a mixture of 3,5-dichloroaniline 1 and diethyl acetylenedicarboxylate (e.g., 2 in tetrahydrofuran (THF) at about 70 °C to afford Michael adduct 3. Reaction B involves heating Michael adduct 3 at about 250 °C in diphenyl ether solvent to afford ethyl 5,7-dichloro-1,4-dihydro-4-oxoquinoline-2-carboxylate ester 4. Ester 4 is then reacted with chlorosulfonyl isocyanate in acetonitrile, followed by quenching with hydrochloric acid (collectively Reaction C) to afford ethyl 4-amino-5,7-dichloro-quinoline-2-carboxylate ester 5, which is then reacted with diphenylcarbamoyl chloride in dimethylformamide (DMF) in the presence of a NaH to afford the DCUKA ethyl ester (Reaction D) or if desired, the DCUKA acid can be isolated by in situ hydrolysis of the ester group. Reaction B in Scheme 1 is a potential impediment to commercial scale production of DCUKA compounds due to the high temperature of the reaction, as well as the expense of the solvent, and the difficulties of purifying the product and recovering the solvent. The processes described herein address this problem.

Scheme 1.

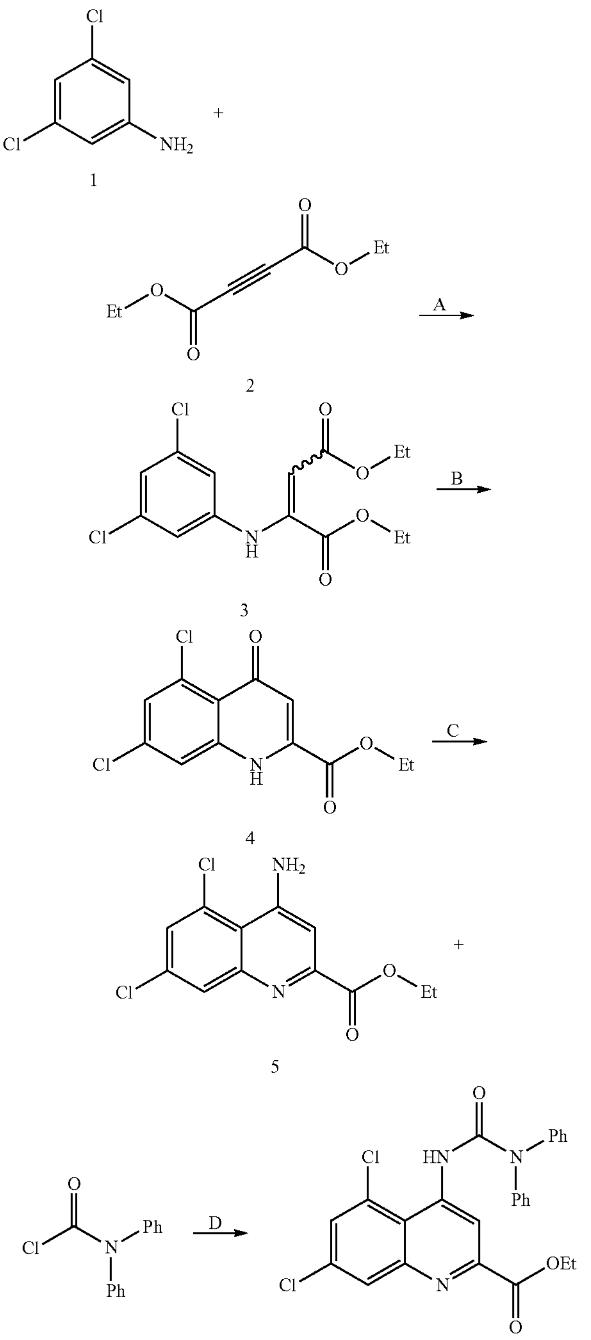

1 2 3 4 5 6

SUMMARY OF THE INVENTION

A method for preparing an alkyl 5,7-dihalo-1,4-dihydro-4-oxoquinoline-2-carboxylate ester of Formula IV, below, is described herein. The method comprises cyclizing a dialkyl 1-(3,5-dihalophenylamino)ethylene-1,2-dicarboxylate compound of Formula III with $P_2O_5$ in methane sulfonic acid (often referred to as Eaton's reagent) in a heated continuous flow reactor to form the alkyl 1,4-dihydro-4-oxoquinoline-2-carboxylate ester of Formula IV. Optionally, a cosolvent such as dichloromethane can be included with the Eaton's reagent. A method of preparing diphenylureido-dihalokynurenic acid esters of Formula VI from the alkyl 5,7-dihalo-1,4-dihydro-4-oxoquinoline-2-carboxylate ester of Formula IV is also described. Diphenylureido-dihalokynurenic acid alkyl esters (e.g., such as DCUKA ethyl ester) are analgesic agents useful in treating chronic pain and alcohol dependence, as well as preventing relapse in alcohol addicted subjects. Scheme 2 summarizes the synthesis of diphenylureido-dihalokynurenic acid alkyl esters of Formula VI according to the methods described herein.

Scheme 2.

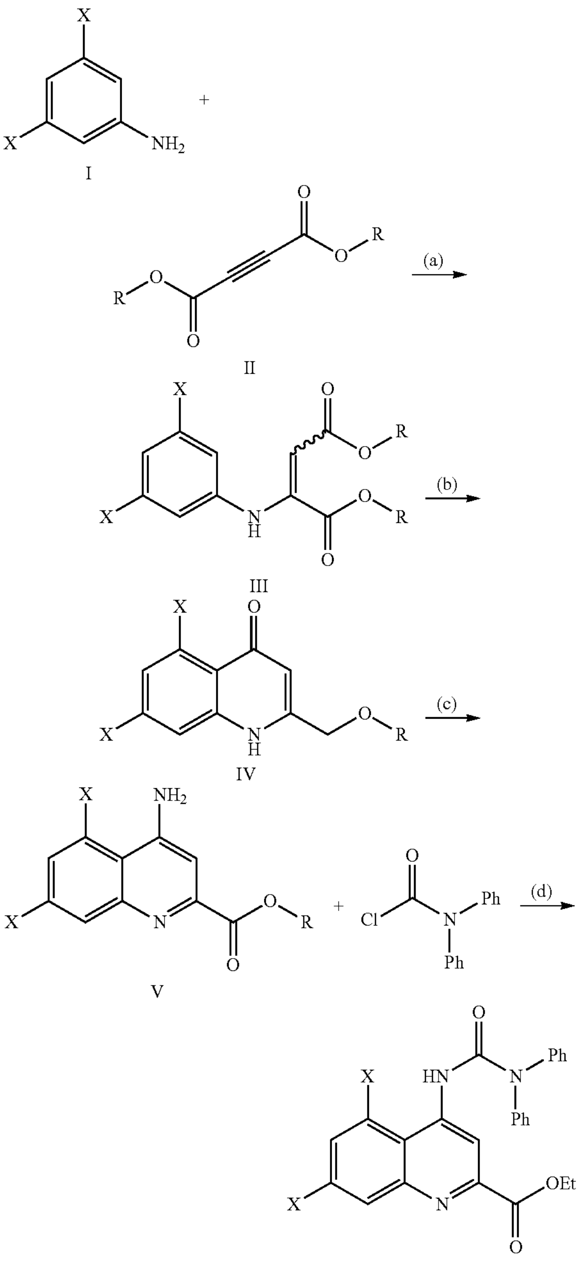

I

II

III

IV

V

VI

In the compounds of Formulas I, II, III, IV, V and VI of Scheme 2, each X independently is a halogen, e.g., F, Cl, Br or I, and each R is a $C_1$ to $C_4$ alkyl group, e.g., methyl (Me), ethyl (Et), propyl (Pr), isopropyl (iPr), butyl (Bu), and the like. In one preferred embodiment, each X is Cl. In another preferred embodiment, each R is ethyl. In yet another preferred embodiment, each X is Cl, and each R is ethyl.

In Scheme 2, Reaction (a) is a Michael addition reaction which typically involves adding the dialkyl acetylenedicarboxylate of Formula II to a heated solution of the 3,5-dihaloaniline of Formula I. The dialkyl 1-arylamino-ethylene-1,2-dicarboxylate Michael adduct of Formula III can be isolated and purified, or can be used in Reaction (b) in crude form.

The previously reported cycloacylation of Compound 3 (Formula III where each X is Cl and each R is ethyl) by Tabakoff et al. is entirely thermally driven by heating a solution of Compound 3 at about 250 °C in a high boiling point solvent such as diphenyl ether (illustrated as Reaction A in Scheme 1). The reaction typically is performed in a bulk reactor, and can be difficult to perform in a flow reactor due to the high temperatures and the relatively low solubility of the product. The high temperature required for the reaction also poses a safety issue, and requires that Compound 3 must be relatively free of unreacted 3,5-dichloroaniline (Compound 1), since any aniline present in the reaction will react with the ester group to form an amide under the high temperature conditions of the reaction.

In the methods described herein, cycloacylation of the Michael adduct of Formula III to form the 1,4-dihydro-4-oxoquinoline compound of Formula IV, Reaction (b) of Scheme 2, is performed at much lower temperature utilizing $P_2O_5$ in methanesulfonic acid (e.g., about 7 to about 10% by weight (wt %) $P_2O_5$ in methanesulfonic acid; also known as Eaton's reagent) than the prior known thermal cycloacylation. As described herein, Reaction (b) is performed in a flow reactor in neat Eaton's reagent as the sole solvent, or with Eaton's reagent and a hydrocarbon or halogenated hydrocarbon cosolvent.

While the use of Eaton's reagent has been reported by Zewge et al. (*J. Org. Chem.,* 2007, 71: 4276-4279) for cycloacylation of aniline derivatives having other substitution patterns on the phenyl ring, the cycloacylation reaction with a 3,5-disubstituted-aniline Michael adduct, such as Compound 3 of Scheme 1, has not been reported or suggested. In fact, Zewge et al. reported (footnote 15) that the cycloacylation of aniline derivatives with Eaton's reagent did not proceed effectively in the presence of cosolvents, and that aniline derivatives with meta substituents provided messy reaction profiles, with a yield of only 30% desired product in the case of a meta-methoxy aniline compound (footnote 22). Thus, the effective cycloacylation of the 3,5-dihaloaniline Michael adducts of Formula III with Eaton's reagent is unexpected. Even more surprising is that a cosolvent can be included with the Eaton's reagent in a flow reaction, given the very negative results reported by Zewge et al. with cosolvents.

Another unexpected advantage of using Eaton's reagent for cycloacylation Reaction (b) is that relatively high levels (up to 25% or more) of unreacted dihaloaniline of Formula I (e.g., Compound 1) can be present during the cycloacylation without significantly interfering with the reaction. Thus, in one preferred embodiment, the isolated crude product of Formula III obtained from the Michael addition, Reaction (a), which contains significant quantities of the unreacted aniline of Formula I, is used in the cycloacylation without further purification, other than isolating the crude product from the solvent used in the Michael addition reaction.

The crude product of Formula IV obtained from the cycloacylation reaction can be isolated by trituration of the product-containing portion of effluent from the flow reactor (e.g., by adding the effluent to chilled water) to obtain the crude 1,4-dihydro-4-oxoquinoline of Formula IV as a granular solid precipitate. The granular solid can then be purified by slurrying the precipitate in a solvent (e.g., acetonitrile, methanol, or isopropanol; preferably isopropanol or acetonitrile) with mild heating (e.g., about 40 °C) to remove impurities into the liquid phase, and then recovering the remaining solids from the slurry (e.g., by filtration) to obtain a substantially purified (90% or greater by high-performance liquid chromatography (HPLC)) compound of Formula IV.

Reaction (c) in Scheme 2 is conversion the 1,4-dihydro-4-oxoquiniline of Formula IV to a 4-aminoquinoline compound of Formula V by reaction of the 1,4-dihydro-4-oxoquiniline compound with chlorosulfonyl isocyanate in an aprotic solvent (e.g., acetonitrile). The crude 4-aminoquinoline product can be purified by slurrying the product in a solvent (e.g., ethyl acetate, ethanol, or isopropanol) with mild heating (e.g., about 50 °C) to remove impurities into the liquid phase, and recovering the remaining solids from the slurry to obtain a substantially purified (>90% by HPLC) compound of Formula V.

Reaction (d) in Scheme 2 is conversion of the 4-aminoquinoline compound of Formula V to the diphenylureido-dihalokynurenic acid ester of Formula VI by reaction with diphenylcarbamoyl chloride in the presence of a base (e.g., sodium hydride) in a polar aprotic solvent (e.g., dimethylacetamide; "DMAc").

The following non-limiting embodiments are provided to illustrate the methods described herein.

A first embodiment is a method for preparing an alkyl 5,7-dihalo-1,4-dihydro-4-oxoquinoline-2-carboxylate ester. The method comprises the sequential steps of:

(i) heating a solution comprising a compound of Formula III dissolved in a reagent comprising about 7 to about 10 wt % $P_2O_5$ in methanesulfonic acid, at a concentration of about 0.15 to about 0.25 grams of the compound of Formula III per mL of the reagent:

III

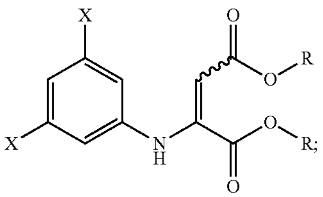

at a selected temperature in the range of about 65 to about 75 °C by pumping the first solution through a heated continuous flow reactor coil at a pumping flow rate sufficient to provide a residence time of about 15 to 40 minutes in the heated coil, and collecting an effluent flowing out of the heated coil comprising an alkyl 5,7-dihalo-1,4-dihydro-4-oxoquinoline-2-carboxylate ester of Formula IV:

IV

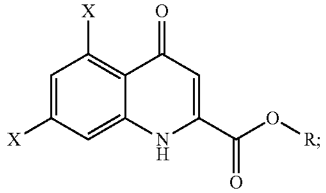

(ii) adding the effluent collected from step (i) to at least about 5 volumes of chilled water per volume of the effluent, with stirring, while maintaining a water temperature of about 15 °C or less, to form a precipitate comprising the ester of Formula IV; and (iii) recovering the precipitate (e.g., by filtration or centrifugation);

wherein in Formula III and Formula IV, each X independently is a halogen atom (e.g., Cl); and each R independently is $C_1$ to $C_4$ alkyl (e.g., Et). Optionally, step (i) can be performed in the presence of a hydrocarbon or halogenated hydrocarbon cosolvent (e.g., dichloromethane).

The method also can include purifying the ester of Formula IV, if desired. The purification is performed by:

(iv) stirring a suspension of the precipitate obtained from step (iii) in a solvent (e.g., about 3 to about 10 mL of the solvent per gram of the precipitate) at a temperature in the range of about 40 to 50 °C for at least about 1 hour; followed by (v) recovering undissolved solid particles comprising a purified ester of Formula IV from the suspension (e.g., by filtration or centrifugation);

wherein the solvent is an organic solvent selected from the group consisting of acetonitrile, methanol, isopropanol, and a combination of two or more thereof. Acetonitrile and isopropanol are preferred solvents for purifying the ester of Formula IV.

A second embodiment is a method for preparing an alkyl 5,7-dihalo-1,4-dihydro-4-oxoquinoline-2-carboxylate comprising the sequential steps of:

(i) contacting a solution comprising about 15 to about 60 wt % of dihaloaniline of Formula I in an aprotic solvent (e.g., tetrahydrofuran (THF), 2-methyl THF, and the like) with at least about 0.9 equivalents of a dialkyl acetylenedicarboxylate of Formula II at a selected temperature of about 70 to about 100 °C for a period of about 6 to about 24 hours to form a compound of Formula III:

I

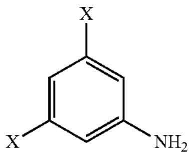

II

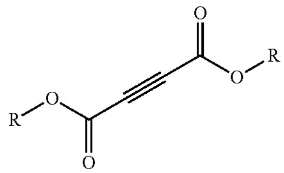

-continued

III

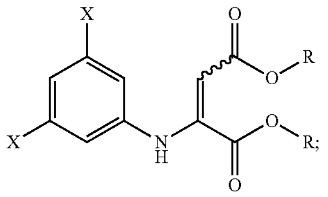

(ii) removing the solvent (e.g., by distillation) to form a residue comprising the compound of Formula III;

(iii) heating a solution comprising the residue from step (ii) dissolved in a reagent comprising about 7 to about 10 wt % $P_2O_5$ in methanesulfonic acid, at a concentration of about 0.15 to about 0.25 grams of the residue per mL of the reagent at a selected temperature of about 65 to about 75 °C by pumping the solution through a heated continuous flow reactor coil at a pumping flow rate sufficient to provide a residence time of about 15 to 40 minutes in the heated coil, and collecting an effluent flowing out of the heated coil comprising an alkyl 5,7-dihalo-1,4-dihydro-4-oxoquinoline-2-carboxylate ester of Formula IV:

IV

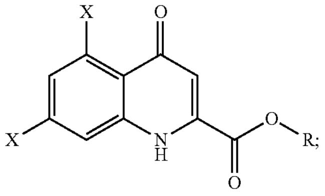

(iv) adding the effluent collected from step (iii) to at least about 5 volumes of chilled water per volume of the effluent, with stirring, while maintaining a water temperature of about 15 °C or less, to form a precipitate comprising the ester of Formula IV; and (v) recovering the precipitate (e.g., by filtration or centrifugation);

wherein in Formula I, Formula II, Formula III, and Formula IV each X independently is a halogen atom (e.g., Cl); and each R independently is $C_1$ to $C_4$ alkyl (e.g., Et). Optionally, step (iii) can be performed in the presence of a hydrocarbon or halogenated hydrocarbon cosolvent (e.g., dichloromethane).

The method of the second embodiment also can include purifying the ester of Formula IV, if desired. The purification is performed by:

(vi) stirring a suspension of the precipitate obtained from step (v) in a solvent (e.g., about 3 to about 10 mL of the solvent per gram of the precipitate) at a temperature in the range of about 40 to 50 °C for at least about 1 hour; wherein the solvent is selected from the group consisting of acetonitrile, methanol, isopropanol, and a combination of two or more thereof; and then (vii) recovering undissolved solid particles comprising a purified ester of Formula IV from the suspension (e.g., by filtration or centrifugation). Acetonitrile and isopropanol are preferred solvents for purifying the ester of Formula IV, as in the first embodiment.

A third embodiment is a method for preparing a diphenylureido-dihalokynurenic acid alkyl ester comprising performing steps (i), (ii), and (iii) of the first embodiment; and then:

(iv) purifying the ester of Formula IV by stirring a suspension of the precipitate obtained from step (iii) in a solvent at a temperature in the range of about 40 to 50 °C for at least about 1 hour; wherein the first solvent is selected from the group consisting of acetonitrile, methanol, isopropanol, and a combination of two or more thereof (acetonitrile and isopropanol are preferred solvents for purifying the ester of Formula IV); and then (v) recovering undissolved solid particles comprising a purified ester of Formula IV from the suspension;

(vi) contacting a solution comprising the purified ester of Formula IV in a polar aprotic solvent (e.g., acetonitrile, THF, 2-methyl-THF) with chlorosulfonyl isocyanate at a temperature of about 40 to about 80 °C until evolution of carbon dioxide gas has ceased;

(vii) adding an acid (e.g., a strong acid such as HCl) in a $C_1$ to $C_4$ alcohol (e.g., methanol, ethanol, isopropanol, propanol, butanol and the like) to the solution from step (vi) and heating the resulting acidic mixture at a temperature of about 65 to about 75 °C. (e.g., about 70 °C) to form a 5,7-dihalo-4-aminoquinoline-2-carboxylate ester of Formula V (preferably the alcohol is selected to have the same alkyl substituent as R):

V

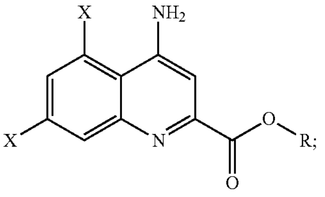

(viii) isolating the ester of Formula V;

(ix) contacting a solution comprising the ester of Formula V isolated in step (viii) in a polar aprotic solvent (e.g., dimethylformamide, dimethylacetamide, N-methylpyrrolidone, propylene carbonate of a combination of two or more thereof) with diphenylcarbamoyl chloride in the presence of a base to form a diphenylureido-dihalokynurenic acid ester of Formula VI:

VI

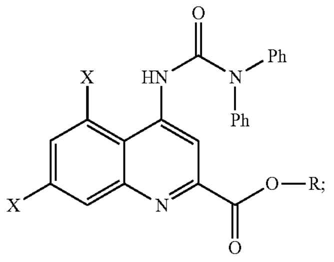

wherein the base is selected from the group consisting of an alkali metal hydroxide (e.g., LiOH, KOH, or NaOH) and an alkali metal hydride (e.g., NaH or KH); preferably the base is NaH (e.g., 60% NaH) or NaOH; and (x) isolating the diphenylureido-dihalokynurenic acid ester of Formula VI; wherein in Formula I, Formula II, Formula III, Formula IV, Formula V, and Formula VI each X independently is a halogen atom (e.g., Cl); and each R independently is a $C_1$ to $C_4$ alkyl (e.g., Et).

Optionally, step (iii) can be performed in the presence of a hydrocarbon or halogenated hydrocarbon cosolvent (e.g., dichloromethane).

The ester of Formula V can be isolated in step (viii) by any desired method. In some embodiments, the ester of Formula V is isolated in step (viii) by adjusting the pH of the acidic mixture of step (vii) to about 9 to about 10 to form a second precipitate comprising the ester of Formula V, which is then recovered, e.g., by filtration or centrifugation.

The method of the third embodiment also can include purifying the ester of Formula V, if desired. The purification is performed by:

(a) stirring a suspension of the ester of Formula V isolated in step (viii) in a solvent (e.g., about 5 to about 10 mL of the solvent per gram of the ester of Formula V) at a temperature in the range of about 40 to 50 °C for at least about 1 hour; wherein the third solvent is selected from the group consisting of a $C_2$ to $C_3$ alcohol (e.g., ethanol or isopropanol), a $C_2$ to $C_3$ alkyl acetate (e.g., ethyl acetate or isopropyl acetate), and a combination thereof;

(b) cooling the suspension of step (a) to a temperature of about 20 to 25 °C, and then recovering undissolved solid particles comprising a purified ester of Formula V from the suspension (e.g., by filtration or centrifugation); Ethanol, isopropanol and ethyl acetate are preferred solvents for purifying the ester of Formula V.

The diphenylureido-dihalokynurenic acid ester of Formula VI can be isolated in step (x) by any desired method. In some embodiments, the ester of Formula VI is isolated in step (x) by adding the solution from step (ix) to about 28 to about 30 volumes of an aqueous acid (e.g., 10 wt % acetic acid) with stirring to form a precipitate comprising the ester of Formula VI, which is then recovered, e.g., by filtration or centrifugation.

If desired, the method of the third embodiment can include purifying the diphenylureido-dihalokynurenic acid ester of Formula VI, as well. The purification is performed by:

(c) forming a solution comprising the ester of Formula VI isolated in step (x) in a solvent that is immiscible with water or a solvent mixture that comprises at least one water-immiscible solvent (e.g., dichloromethane, ethyl acetate/ethanol mixture, methyl-t-butyl ether, 2-methyl-THF), and sequentially washing the solution with an aqueous base, followed by an aqueous acid;

(d) removing any remaining solvent from the solution of step (c) to recover a residue comprising ester of Formula VI;

(e) stirring a suspension of the residue from step (d) in a solvent (e.g., about 5 to about 10 mL of the solvent per gram of the residue) at a temperature in the range of about 40 to 50 °C for at least about 1 hour; wherein the solvent comprises one or more $C_2$ to $C_3$ alcohol (e.g., ethanol, propanol, or isopropanol); and (f) cooling the suspension from step (e) to a temperature of about 20 to 25 °C, and then recovering undissolved solid particles comprising a purified ester of Formula VI from the suspension (e.g., by filtration or centrifugation). Ethanol and isopropanol are preferred solvents for purifying the ester of Formula VI.

A fourth embodiment is a method for preparing a diphenylureido-dihalokynurenic acid alkyl ester comprising performing steps (i), (ii), (iii), (iv), and (v) of the second embodiment; and then:

(vi) purifying the ester of Formula IV by stirring a suspension of the precipitate obtained from step (v) in a solvent at a temperature in the range of about 40 to 50 °C for at least about 1 hour, wherein the second solvent is selected from the group consisting of acetonitrile, methanol, isopropanol, and a combination of two or more thereof;

(vii) recovering undissolved solid particles comprising a purified ester of Formula IV from the suspension of step (vi);

(viii) contacting a solution comprising the purified ester of Formula IV with chlorosulfonyl isocyanate in a polar aprotic solvent (e.g., acetonitrile) at a temperature of about 40 to about 80 °C until evolution of carbon dioxide gas has ceased;

(ix) adding a strong acid (e.g., HCl) in a $C_1$ to $C_4$ alcohol (e.g., methanol, ethanol, isopropanol, propanol, butanol, and the like) to the solution of step (viii) and heating the resulting acidic mixture at a temperature of about 65 to about 75 °C. (e.g., about 70 °C) to form a 5,7-dihalo-4-aminoquinoline-2-carboxylate ester of Formula V (preferably the alcohol is selected to have the same alkyl substituent as R):

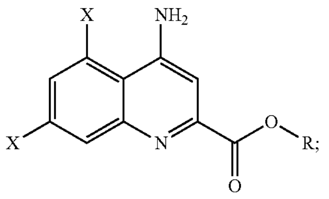

V (x) isolating the ester of Formula V;

(xi) contacting a solution comprising the ester of Formula V isolated in step (x) in a polar aprotic solvent (e.g., dimethylformamide, dimethylacetamide, N-methylpyrrolidone, propylene carbonate of a combination of two or more thereof) with diphenylcarbamoyl chloride in the presence of a base to form a diphenylureido-dihalokynurenic acid ester of Formula VI:

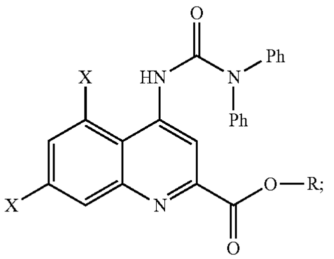

VI wherein the base is selected from the group consisting of an alkali metal hydroxide (e.g., LiOH, KOH, or NaOH) and an alkali metal hydride (e.g., NaH or KH); preferably the base is NaH (e.g., 60% NaH) or NaOH; and (xii) isolating the diphenylureido-dihalokynurenic acid ester of Formula VI;

wherein in Formula I, Formula II, Formula III, Formula IV, Formula V, and Formula VI each X independently is a halogen atom (e.g., Cl); and each R independently is a $C_1$ to $C_4$ alkyl (e.g., Et). Optionally, step (v) can be performed in the presence of a hydrocarbon or halogenated hydrocarbon cosolvent (e.g., dichloromethane). In some embodiments a combination of 75% ethyl acetate and 25% methyl ethyl ketone (v/v) was a surprisingly effect solvent for dissolving compounds of Formula (VI) for purification, without using dichloromethane.

The ester of Formula V can be isolated in step (x) by any desired method. In some embodiments, the ester of Formula V is isolated in step (x) by adjusting the pH of the acidic mixture of step (ix) to about 9 to 10 to form a second precipitate comprising the ester of Formula V, which is then recovered, e.g., by filtration or centrifugation.

The method of the fourth embodiment also can include purifying the ester of Formula V, if desired. The purification is performed by:

(a) stirring a second suspension comprising the ester of Formula V isolated in step (x) in a solvent (e.g., about 5 to about 10 mL of the solvent per gram of the ester of Formula V) at a temperature in the range of about 40 to 50 °C for at least about 1 hour; wherein the solvent is selected from the group consisting of a $C_2$ to $C_3$ alcohol (e.g., ethanol or isopropanol), a $C_2$ to $C_3$ alkyl acetate (e.g., ethyl acetate or isopropyl acetate), and a combination thereof (preferably ethanol, isopropanol, or ethyl acetate);

(b) cooling the suspension from step (a) to a temperature of about 20 to 25 °C, and then recovering undissolved solid particles comprising a purified ester of Formula V from the suspension (e.g., by filtration or centrifugation).

The diphenylureido-dihalokynurenic acid ester of Formula VI can be isolated in step (xii) by any desired method. In some embodiments, the ester of Formula VI is isolated in step (xii) by adding the solution from step (xi) to about 26 to about 30 volumes of an aqueous acid (e.g., 10 wt % acetic acid) with stirring to form a precipitate comprising the ester of Formula VI, which is then recovered, e.g., by filtration or centrifugation.

If desired, the method of the third embodiment can include purifying the diphenylureido-dihalokynurenic acid ester of Formula VI, as well. The purification is performed by:

(c) forming a solution comprising the ester of Formula VI isolated in step (xii) in a solvent that is immiscible with water (e.g., dichloromethane, ethyl acetate, methyl-t-butyl ether, methyl ethyl ketone; combinations thereof, and the like), and sequentially washing the solution with an aqueous base, followed by an aqueous acid;

(d) removing the solvent from step (c) to recover a residue comprising ester of Formula VI; and (e) stirring a suspension of the residue from step (d) in a solvent (e.g., about 5 to about 10 mL of the fifth solvent per gram of the second residue) at a temperature in the range of about 40 to 50 °C for at least about 1 hour; wherein the solvent comprises one or more $C_2$ to $C_3$ alcohol (e.g., ethanol, propanol, or isopropanol; preferably ethanol or isopropanol); and (f) cooling the suspension of step (e) to a temperature of about 20 to 25 °C, and then recovering undissolved solid particles comprising a purified ester of Formula VI from the suspension (e.g., by filtration or centrifugation).

If desired, the purified ester of Formula VI can be converted to the corresponding carboxylic acid (e.g., to DCUKA) or to a salt thereof by hydrolysis. In addition, the carboxylic acid or the carboxylate salt can be converted to an addition salt with a strong acid, such as p-toluenesulfonic acid, such that the heterocyclic nitrogen of the diphenylureido-dihalokynurenic acid is protonated.

In another aspect, improved methods of preparing diphenylureido-dihalokynurenic acids, and tosylate addition salts thereof are provided, which involve direct conversion of esters of Formula V to diphenylureido-dihalokynurenic acids of Formula VIII and tosylate addition salts of Formula IX. As used herein, "direct conversion" means that intermediate products formed at each reaction step are not purified before proceeding to the next step other than filtering and washing precipitated crude intermediates in some or all of the steps. Scheme 3 illustrates this direct route from compounds of Formula V to compounds of Formula IX.

Scheme 3.

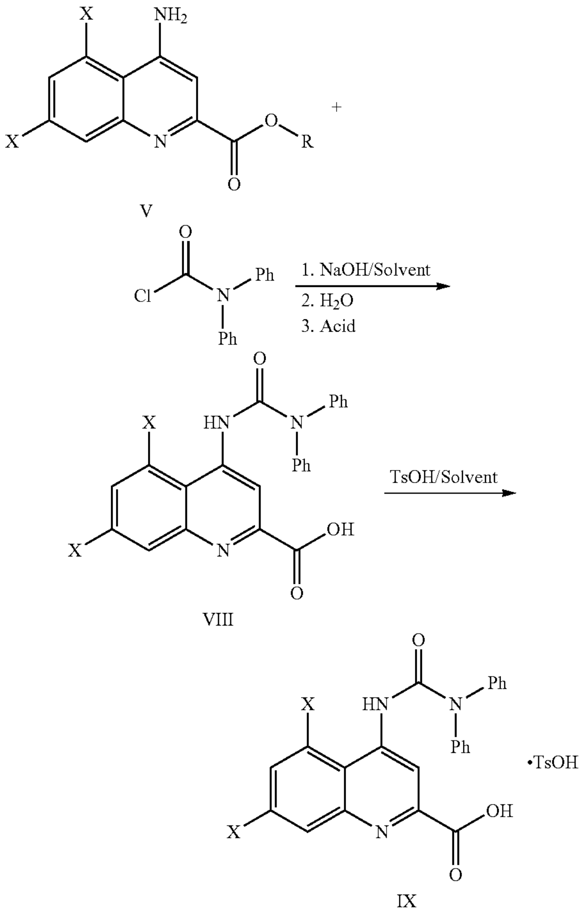

V

VIII

IX

In Scheme 3, amino ester V is directly converted to acid VIII by successive reactions with (1) diphenyl carbamoyl chloride and an excess of sodium hydroxide (solid, preferably powdered, and preferably about 3 molar equivalents) in a polar aprotic solvent (e.g., DMAc) to form a urea intermediate compound of Formula VI as described herein above; (2) after reaction (1) is complete, adding water to the reaction mixture, so that the excess sodium hydroxide hydrolyzes the ester group to form a sodium carboxylate salt of Formula VII, as described herein below; and (3) after the hydrolysis reaction (2) is complete, adding an aqueous acid to the reaction mixture (e.g., aqueous acetic acid) to convert the carboxylate salt to the carboxylic acid Formula VIII. The carboxylic acid of Formula VIII is then converted to the tosylate addition salt by reaction with an excess of aqueous toluenesulfonic acid (TsOH; e.g., 3M) in a suitable solvent (e.g., ethyl acetate). The product can be isolated by filtration after the addition salt precipitates. In Scheme 3, each X is a halogen, e.g., F, Cl, Br or I; each R is a $C_1$ to $C_4$ alkyl group, e.g., methyl, ethyl, propyl, isopropyl, butyl, and the like; and M is Na. In one preferred embodiment, X is Cl. In another preferred embodiment, R is ethyl. In yet another preferred embodiment, X is Cl, and R is ethyl.

This process constitutes a convenient direct synthesis route for conversion of 4-amino-5,7-dihaloquinoline-2-carboxylate esters (i.e., Formula V) to diphenylureido-dihalokynurenic acids (Formula VIII) and their tosylate addition salts (Formula IX). By not isolating and purifying intermediate products of Formulas VI and VII, and using NaOH as the base for the carbamylation reaction, the final yield and purity of the addition salt of Formula IX (e.g., DCUKA tosylate) is surprisingly and significantly improved over the process using NaH as base and in which each compound to isolated an purified along the reaction pathway, as is, of course, the yield and purity of the acid of Formula VIII (e.g., DCUKA). Sodium hydroxide pellets are effective as the base for carbamylation of 4-amino-5,7-dihaloquinoline-2-carboxylate esters with diphenyl carbamoyl chloride; however, sodium hydroxide pellets can stick to the reactor sides in some case, interfering with stirring. Use of powdered sodium hydroxide is advantageous to reduce or eliminate adherence of the sodium hydroxide to the sides of the reactor.

BRIEF DESCRIPTION OF THE DRAWINGS

FIG. 1 Schematically illustrates a flow reactor for use in the methods described herein.

DETAILED DESCRIPTION OF PREFERRED EMBODIMENTS

As noted above, the previously reported procedures for the synthesis of DCUKA ethyl and methyl esters, illustrated in Scheme 1 for the ethyl ester, involves four stages, beginning with the treatment of 3,5-dichloroaniline 1 with a diethyl acetylenedicarboxylate 2 in THF under reflux conditions to obtain Michael adduct 3, which then is thermally cyclized at 250 °C in diphenyl ether ($Ph_2O$) to afford ethyl 5,7-dichloro-1,4-dihydro-4-oxoquinoline-2-carboxylate ester 4. Ester 4 is then treated with chlorosulfonyl isocyanate under reflux conditions to provide 4-aminoquinoline 5. The amino group of Compound 5 is then reacted with diphenylcarbamoyl chloride in the presence of NaH in DMF to afford the target DCUKA ethyl ester 6. Ester 6 and the corresponding acid (where the ethyl group, Et, is replaced by H) are analgesics, which are useful for treating chronic pain and alcohol dependence, as well as other related conditions.

A significant advance in the synthesis of DCUKA esters is described herein, which comprises the use of a solution of diphosphorus pentoxide in methane sulfonic acid (also known as Eaton's reagent) for the cycloacylation reaction, which eliminates the requirement of high temperature in the cycloacylation reaction and is amenable to use in flow reactor conditions.

Aza-Michael Reaction (Reaction (a) of Scheme 2).

As illustrated by the preparation of Compound 3 (Formula III in which each X is Cl and each R is Et), the aza-Michael reaction is carried out by dropwise addition of a THF solution of about 1.1 equivalents (eq) of diethyl acetylenedicarboxylate 1 to a THF solution of about 1 eq of 3,5-dichloroaniline 2, and then heating the resulting mixture at about 70 °C for several hours (h), e.g., about 4 to 7 hours, to produce a crude Michael addition product 3 as a mixture of cis and trans isomers. Compound 3 has been obtained at a conversion of about 75% (based on consumption of 3,5-dichloroaniline 1) under these conditions, which did not improve upon heating the reaction for 24 h. As described elsewhere herein, conversions were determined by HPLC area under curve (AUC) measurements, unless otherwise specified. The conversion to Compound 3 can be increased to about 98% by addition of another 0.5 eq of the diethyl acetylenedicarboxylate and additional heating at 70 °C for about 22 h. However, diethyl acetylenedicarboxylate is not thermally stable and decomposes with a significant energy release, so it is preferable to limit the diethyl acetylenedicarboxylate charge to less than one equivalent (e.g., about 0.9 eq) for safety purposes. Upon consumption of about 75% of the 3,5-dichloroanilne (as determined by HPLC), THF was removed by distillation and the crude Michael adduct mixture can be directly used in the subsequent cycloacylation reaction to produce Compound 4, as described below. This procedure was found to be suitable for the production of the Michael adduct material in a multi-kilo scale.

Cycloacylation (Reaction (b) of Scheme 2).

The cycloacylation step to form a compound of Formula IV, such as Compound 4 (Formula IV where x is Cl and R is Et) was originally carried out at 250 °C in diphenyl ether. Attempts at performing this reaction in a continuous flow reactor under such conditions, to provide a more practical large-scale synthesis, led to partial precipitation of the cyclized product from the diphenyl ether into the reactor lines causing hazardous conditions due to high back pressure. To circumvent this problem, alternative cycloacylation methods were considered.

The cycloacylation and compatibility of compounds of Formula III (e.g., Compound 3) to highly acidic Eaton's reagent was investigated at a small scale by bulk reaction of Compound 3 with neat Eaton's reagent at a concentration of about 4-6 mL of Eaton's reagent per gram of Compound 3 (also referred to 4-6 volumes of Eaton's reagent, for convenience). The reaction was performed at 60 °C, while following the reaction by HPLC. The HPLC results showed the consumption of Compound 3 with the formation of a new peak without significant byproducts.

With success in a small-scale bulk cycloacylation, the procedure was examined under flow conditions and optimized further. The cycloacylation of Compound 3 (which has two meta-chloro substituents) with neat Eaton's reagent proceeded surprisingly well under flow conditions, even with crude Compound 3 containing 20-25% unreacted dichloroaniline (Compound 1). The flow reaction provided significantly higher conversions of (e.g., 85-95% based on the initial amount of Compound 3) in comparison to a bulk cycloacylation reaction of Compound 3, which provided only about 75% conversion after heating for about 2 h, with no further increase in conversion thereafter. Unexpectedly, cosolvents (e.g., dichloromethane) did not significantly interfere with the cycloacylation reaction under flow conditions, in contrast to the results reported by Zewge et al. (footnote 15), which indicated that cosolvents all but shut down the reaction, at least at the 20-hour reaction timeframe examined.

Advantageously, crude Compound 3, comprising about 75 mol % of 3 and about 20 to 25% of unreacted 3,5-dichloroaniline 1, can be utilized in the cycloacylation with Eaton's reagent without significant interference from the unreacted aniline compound. For example, in a reaction utilizing about 10 grams of crude Compound 3 dissolved in about 40 mL (4 volumes) of Eaton's reagent at 70 °C, with a 20 min residence time and a backpressure of about 15 pounds per square inch (psi), afforded crude product comprising about 73% of 4 and about 22% 3,5-dichloroaniline based on AUC measurements from HPLC data, indicating a very high conversion of Compound 3 in the crude starting material to Compound 4 (e.g., greater than 95%).

As noted above, under flow reactor conditions, the cycloacylation reaction also proceeds surprisingly well with cosolvents added to Eaton's reagent. This is in stark contrast to reported attempts at similar cycloacylations using Eaton's reagent with a cosolvent (toluene, xylene and sulfolane) in bulk reactions at 1:1 and 2:1 ratios of solvent to Eaton's reagent, which were reported Zewge et al. to be very sluggish, with best conversion being only about 3% after 20 h at 100 °C with 1:1 toluene/Easton's reagent (Zewge et al. footnote 15).

Isolation of Compounds of Formula IV. As illustrated by the reaction of crude Compound 3 with Eaton's reagent to produce Compound 4, the crude product from the cycloacylation reaction (Reaction (b) of Scheme 2) can be readily isolated as a granular solid by trituration, e.g., by adding the product-containing effluent to cold (e.g., 0 to 15 °C) water (typically about 5 to 20 volumes of water per volume of effluent) with vigorous stirring (typically over a period of several minutes to several hours) to precipitate the product, followed by filtering to recover the precipitate, and drying the recovered precipitate under vacuum. Optionally, the water can include a base to neutralize or partially neutralize the methane sulfonic acid and any phosphoric acid that may form upon adding the effluent to the water. The trituration procedure can be used even when a cosolvent such as dichloromethane is present in the effluent.

The crude precipitate, which may still contain some unreacted Compound 3, significant amounts of unreacted 3,5-disubstituted aniline 1, as well as some side products, can be further purified by slurring crude Compound 4 in an aqueous solution of a basic salt such as sodium acetate (e.g., about 5 to 20 mL of aqueous salt solution per gram of crude Compound 4). Alternatively, or in addition, the crude Compound 4 can be purified by slurrying the solid in an organic solvent in which the product has moderate to low solubility, such as a $C_1$-$C_3$ alcohol (e.g., methanol or isopropanol) or acetonitrile. With isopropanol and acetonitrile, purities of up to 95% can be achieved, with recoveries of up to 90% of the theoretical amount of desired product in the crude solid product.

Amination (Reaction (c) of Scheme 2).

With high quality Compound 4 in hand, evaluation of the amination reaction was initiated. Chlorosulfonyl isocyanate was added to a suspension of Compound 4 in acetonitrile at 23 °C. Although chlorosulfonyl isocyanate is one of the most reactive isocyanates according to literature, there was no exotherm observed during the addition. After completion of addition, the mixture was heated to reflux (about 75-80 °C), for about 1 h during which the reaction was followed by HPLC. Upon reaching a temperature of about 40-45 °C, the reaction mixture became a clear brown solution and a continuous evolution of $CO_2$ was observed, which ceased at a temperature of about 65-70 °C. A new broad peak appeared in the HPLC profile, with concomitant consumption of Compound 4. At this point, the mixture was cooled to about 35-40 °C and 1.5 M HCl in methanol was added, followed by heating to reflux at about 70 °C for an additional 1 h to quench the intermediate product formed in the initial reaction and to release the 4-aminoquinoline product, Compound 5. The appearance of a new peak in the HPLC profile, with the disappearance of the wide peak confirmed the progress of the reaction to release the product.

Isolation of Compounds of Formula V. As part of initial optimization, 0.5 N NaOH was added to the reaction mixture directly at 0-5 °C to adjust the pH of the mixture to about 9-10, as measured by a pH meter. The resulting thick slurry was filtered and washed with water to collect the tan colored filter cake, which was conditioned at 40-45 °C. The HPLC purity of the filter cake was assessed as about 88% with no loss of product in filtrate and washes.

Some ester exchange from ethyl to methyl was observed with HCl in methanol, so the procedure was modified by using HCl-ethanol, instead. Thus, it is preferable that the alcohol used for the quenching solution have the same alkyl group as the ester in the reaction product. To enhance process safety, chlorosulfonyl isocyanate preferably is added to a solution of Compound 5 at about 70 °C instead of 23 °C, which results in controlled evolution of $CO_2$ during the entire addition. Following this procedure, crude Compound 5 is isolated in up to 93% yield at a purity of up to 90%.

Purification of Crude Compounds of Formula V. Crude Compound 5 was readily purified by slurrying in a variety of solvents, including ethanol, isopropanol and ethyl acetate. For examples, slurrying in 3 to 5 volumes of isopropanol (i.e., 3 to 5 mL per gram of crude product) resulted in a recovery of about 85% of Compound 5 at purities of 94 to 97% as determined by HPLC. Similar results were obtained with 3 to 5 volumes of ethanol, albeit with slightly lower recovery (64-72%) and slightly higher purity (98 to 99%). Slurry purification with about 3 to 10 volumes ethyl acetate afforded the highest recoveries (88 to 90%) at HPLC purities of 93 to 97%.

Carbamylation (Reaction (d) in Scheme 2).

The carbamylation of Compounds of Formula V to form the diphenylureido-dihalokynurenic acid esters of Formula VI is illustrated by the conversion of Compound 5 to form DCUKA ethyl ester 6. The carbamylation is carried out in a polar aprotic solvent such as dimethylformamide (DMF), dimethylacetamide (DMAc), N-methylpyrrolidone (NMP), propylene carbonate (PC), and the like, by addition of diphenylcarbamoyl chloride to a solution of the compound of Formula V, e.g., Compound 5, in the presence of a an alkali metal hydroxide such as NaOH, or an alkali metal hydride such as NaH. DMAc is a preferred solvent for the reaction, and 60% sodium hydride is the preferred base.

A number of bases were evaluated for the reaction. Lithium and sodium hexamethyldisilazine (LiHMDS and NaHMDS) in THF solvent both led to loss of Compound 5 as determined by HPLC, but without formation of the desired DCUKA ethyl ester Compound 6, instead the acid form of Compound 5 (where Et is replaced by H) was formed. Similar results were observed with potassium tert-butoxide and sodium ethoxide. Weaker bases such as pyridine, diisopropylethylamine in toluene, and cesium carbonate in DMF also failed to afford the desired product, as did neat pyridine.

The use of NaH in THF also was unsuccessful, while reactions were effective in DMF, DMAc, NMP and propylene carbonate (PC). Use of NaOH and LiOH in DMAc did result in formation of Compound 6, with NaOH providing 85 to 90% conversion, although a longer reaction time (16 h) was required. LiOH provided only 25% conversion in DMAc. Overall, the use of 60% NaH in DMAc solvent provided a reduced reaction time, the highest conversion, and the best safety for large scale batches, since DMAc is essentially inert in presence of NaH. In summary, 60% NaH with DMAc provided the desired product in over 95% conversion within 1 h after the complete addition of the base.

Isolation and Purification of Compounds of Formula VI. Upon completion of the carbamylation reaction, as confirmed by HPLC, quench methods were evaluated. Initially the reaction mixture was slowly charged into cold water (0 to 5 °C) for the precipitation of product. While this procedure does work, some hydrolysis of the ester group can occur, so it is desirable to quench the reaction in an acidic solution, such as 10 wt % acetic acid (AcOH) to avoid hydrolysis of ethyl ester in Compound 6. The crude yield of the product, after filtration to recover the filter cake consistently was about 85 to 90% with about 85 to 90% purity by HPLC. To remove the byproduct DCUKA acid that is formed during the reaction, acid/base workup followed by crystallization or a slurry wash purification was developed. For example, the crude filter cake can be dissolved in about 10 volumes of dichloromethane (DCM) and washed with about 3 volumes of 0.5 M NaOH solution followed by about 3 volumes of 0.3 M citric acid solution, which removes some of the impurities observed in the HPLC. Alternatively, 60 volumes of 75%/25% v/v EtOAc/MEK can be used to dissolve the crude DCUKA acid, in place of DCM.

As alternatives, a crystallization method and a slurry purification method were developed to purge two unknown impurities observed in the crude product. Slurry purification with isopropanol (IPA) and ethanol (EtOH) was effective at removing the impurities with good overall recovery. Upon removal of DCM to dryness, the crude Compound 6 was suspended in about 10 volumes IPA or EtOH and slurried at 40 °C overnight, followed by cooling to 23 °C. Filtration led to highly pure (>98%) Compound 6 from both IPA and EtOH, and the $^1$H-NMR spectra exhibited no additional peaks except solvents.

Crystallization initiated by a solvent swap from DCM to EtOH also provided high purity Compound 6, since this material is relatively insoluble in EtOH. Alternatively, a mixture of EtOAc and MEK can be used to dissolve the crude DCUKA acid, and this solvent combination can be removed by solvent swapping with EtOH as in the case of DCM. The organic phase was subjected to distillation at 45 °C to reduce the DCM volume level about 4- to 5-fold from initial volume, and then EtOH was added dropwise continuously to remove DCM further during the distillation. After about 6 volumes of EtOH was added, the mixture was maintained at about 70 °C for about 45 min to afford a DCM to EtOH ratio of about 1:22 as determined by $^1$H-NMR analysis. The resulting slurry was slowly cooled to 20 °C and maintained at 20 °C overnight. Filtration followed by HPLC analysis of filter cake confirmed the complete removal of both impurities. Overall the isolation and purification methods afforded Compound 6 in in about 65% recovery with >98% purity.

As yet another alternative, DCM can be eliminated from the crystallization process for the compounds of Formula VI (e.g., Compound 6). Several solvents were screened to replace DCM, including EtOAc/EtOH, EtOAc/THF, EtOAc/MEK. A solvent ratio of 80/20 to 60/40 was screened. From all the screened solvents only EtOAc/MEK was successful to dissolve Compound 6 at 50 vol, with a 75/25 ratio of EtOAc/MEK.

Hydrolysis of Compounds of Formula VI to Form Acids of Formula VII. Compounds of Formula VI can be hydrolyzed to the corresponding salt of Formula VII or the acid of Formula VIII:

VII

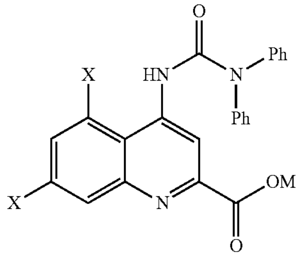

VIII

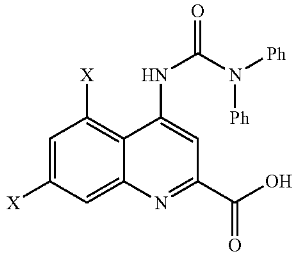

where M is a cation (e.g., $Na^+$). The salt of Formula VII is formed by base hydrolysis in an aqueous solvent (e.g., a mixture of water and an alcohol) followed by adjusting the pH to about 5 to precipitate the salt. For example, addition of a base such as sodium hydroxide (e.g., 2 eq) to an aqueous solution (e.g., a water-alcohol mixture) of Compound 6 with mild heating (e.g., 50 °C) resulted in complete hydrolysis to the salt Compound 7 (Formula VII where each X is Cl and M is Na). Adjusting the pH to about 5 with a mild acid (e.g., acetic acid) results in precipitation of the salt from the solution. Compound 7 can then be isolated by filtration, and purified by slurrying the filtrate with an alcohol (e.g., methanol) and with water. The carboxylic acid of Formula VIII (e.g., DCUKA) can too be formed from the salt of Formula VII by neutralization with a strong acid.

If desired, addition salts of diphenylureido-dihalokynurenic acids can be formed by treating the salt of Formula VII with an excess of a strong acid, such asp-toluenesulfonic acid (TSOH), to form the addition salt of Formula IX:

IX

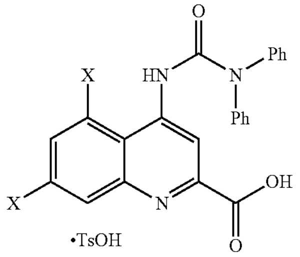

wherein X is a halogen. For example, addition of 2 equivalents of TsOH to a solution of Compound 7 resulted in formation of the TsOH addition salt, Compound 8, at very high conversions (up to about 100%).

A Flow Reactor Design for Cycloacylation.

FIG. 1 schematically illustrates a reactor 10 for performing the cycloacylation reaction. Reactor 10 comprises a flow pipe 12 having influx section 14, conditioning coil section 22, reactor coil section 24, and efflux section 26. Influx section 14 is in fluid flow connection with pump 18, which is in fluid flow connection with conditioning coil section 22. Conditioning coil section 22 is in fluid flow connection with reactor coil section 24. Conditioning coil section 22 and reactor coil section 24 are housed within heated chamber 20. Reactor coil section 24 is in fluid flow connection with efflux section 26. In operation, a reaction mixture is charged into reactant reservoir 16 and is drawn into pump 18 via influx section 14 of pipe 12, and expelled from pump 18 into conditioning coil section 22, where the reaction mixture them flows into reactor coil section 24, and then out of heated chamber 20 via efflux section 26 of pipe 12 into effluent reservoir 28.

In use, flow of the reaction mixture is in the direction of broad arrows A. Heated chamber 20 is heated to a temperature sufficient to heat the contents of reactor coil section 24 to a desired reaction temperature. The total internal volume of conditioning coil section 22 and reactor coil section 24, in combination with the pumping rate of pump 18, are selected to afford a desired residence time for the reaction mixture within heated chamber 20. Typically, pipe 12 is initially filled with a reaction solvent, which is displaced by the reaction mixture as pumping proceeds. Effluent that does not contain any of the product from the cycloacylation reaction typically is discarded before collecting effluent containing the product. In order to maintain pumping efficiency, reactant reservoir 16 is refilled as needed, or alternatively, additional reactant reservoirs can be connected to pump 18 as one reservoir is depleted. In the final stage of operation, solvent can be pumped through pipe 12 to displace the last remaining reaction mixture through the reactor.

In another aspect, improved methods of converting 4-amino-5,7-dihaloquinoline-2-carboxylate esters (i.e., Formula V) to diphenylureido-dihalokynurenic acids (Formula VIII) and their tosylate addition salts (Formula IX) are provided. In one embodiment, the method involves direct conversion of esters of Formula V to tosylate addition salts of Formula IX. Scheme 3, described above, illustrates this direct route from the amino ester of Formula V to the tosylate addition salt of Formula IX.

In Scheme 3, the 4-amino-5,7-dihaloquinoline-2-carboxylate ester of Formula V is converted to a diphenylureido-dihalokynurenic acid of Formula VIII without isolation and purification of intermediate products, other than filtering and washing the filter cakes. In a first step, an amino ester of Formula V is reacted with diphenyl carbamoyl chloride and an excess of solid sodium hydroxide (preferably about 2 to about 4 molar equivalents of NaOH, e.g., about 3 molar equivalents) in a polar aprotic solvent, such as DMAc, DMF, acetamide, NMP, and the like, to form diphenylureido-dihalokynurenic ester of Formula VI as an intermediate product, which is not isolated. After the carbamylation reaction is complete, water is added to the reaction mixture, so that the excess sodium hydroxide and water together hydrolyze the ester group to form a sodium salt of diphenylureido-dihalokynurenic acid of Formula VII (in which M is Sodium), which also preferably is not isolated. After the hydrolysis reaction is complete, an aqueous carboxylic acid (e.g., a carboxylic acid such as acetic acid) is added to achieve a slightly acidic pH (e.g., a pH in the range of about 6 to about 7.5) to form the diphenylureido-dihalokynurenic acid of Formula VIII, which is isolated by precipitation and filtration, and is washed with water to remove soluble impurities. The crude, isolated diphenylureido-dihalokynurenic acid is then dissolved in an organic solvent and an excess of aqueous (e.g., about 1 to 3 M) toluenesulfonic acid (TsOH; e.g., about 1.1 to 1.5 equiv.; preferably about 1.2 equiv.) is added to the solution to form the tosylate addition salt of Formula IX. Preferably, the organic solvent is a solvent in which the addition salt is insoluble or has low solubility, such as an alkyl ester (e.g., ethyl acetate), an alcohol (e.g. ethanol, methanol), and/or an ether (e.g., tert-butylmethyl ether) so that the product salt will precipitate for ease of isolation.

This process for preparing the tosylate addition salts has significant advantages. By not purifying intermediate products of Formulas VI, VII and VIII, and using NaOH as the base for the carbamylation reaction, the final yield and purity of the addition salt of Formula IX, is surprisingly and significantly improved over the alternative process described herein using NaH as base for the carbamylation reaction, and in which each intermediate product in the reaction pathway (e.g., compounds of Formula VI, VII and VIII) are isolated and purified.

Accordingly, in one embodiment, a method of preparing diphenylureido-dihalokynurenic acid comprises the sequential steps of.

(a) adding an excess of solid sodium hydroxide to a stirring solution of diphenyl carbamoyl chloride and a 4-amino-5,7-dihalo-quinoline-2-carboxylic ester of Formula V in a polar aprotic solvent, and stirring the resulting mixture until carbamylation of the amino group of the 4-amino-5,7-dihalo-quinoline-2-carboxylic ester is complete, thereby forming a solution of a diphenylureido-dihalokynurenic ester of Formula VI;

(b) adding water to the solution of the diphenylureido-dihalokynurenic ester from step (c), and stirring the resulting solution until hydrolysis of the ester group thereof is complete, thereby forming a diphenylureido-dihalokynurenic acid sodium salt of Formula VII; and adjusting the pH of the reaction mixture to about 6 with an acid;

(c) filtering the pH adjusted precipitate of step (b), and washing the filter cake comprising sodium salt of Formula VII with water;

(d) adding a sufficient amount of an aqueous carboxylic acid (e.g., acetic acid) to the filter cake of step (c) to achieve a pH in the range of about 6 to about 7 and stirring the resulting slurry of a diphenylureido-dihalokynurenic acid of Formula VIII until conversion of the sodium salt to the diphenylureido-dihalokynurenic acid is complete;

(e) filtering the slurry from step (d), and washing the filter cake comprising the diphenylureido-dihalokynurenic acid of Formula VIII with water to remove water soluble impurities therefrom;

(g) isolating the diphenylureido-dihalokynurenic acid (e.g., by filtration);

wherein:

X is halogen;

M is Na, and

R is a $C_1$ to $C_4$ alkyl group.

Completeness of the various reactions described herein can be determined by high performance liquid chromatography (HPLC) as described in the examples, below, by monitoring the loss of a limiting reagent, such as the compounds of Formulas V, VI, VII, and VIII, as the case may be.

In some embodiments of the method for preparing diphenylureido-dihalokynurenic acids Formula VIII, the solid sodium hydroxide (preferably powdered sodium hydroxide) in step (a) is added while maintaining a temperature below about 5 °C, and then after completing the addition, stirring the mixture at about 20±5 °C until carbamylation of the amino group of the 4-amino-5,7-dihalo-quinoline-2-carboxylic ester is complete.

In some embodiments of the method for preparing diphenylureido-dihalokynurenic acids Formula VIII, the water is added in step (b) while maintaining a temperature of about 30±5 °C, and the mixture is then stirred at a temperature in the range of about 20 to 45 °C until hydrolysis of the ester group is complete.

In another embodiment, a method of preparing diphenylureido-dihalokynurenic acid tosylate addition salts comprises the sequential steps of:

(a) adding an excess of solid sodium hydroxide to a stirring solution of diphenyl carbamoyl chloride and a 4-amino-5,7-dihalo-quinoline-2-carboxylic ester of Formula V in a polar aprotic solvent, and stirring the resulting mixture until carbamylation of the amino group of the 4-amino-5,7-dihalo-quinoline-2-carboxylic ester is complete, thereby forming a solution of a diphenylureido-dihalokynurenic ester of Formula VI;

(b) adding water to the solution of the diphenylureido-dihalokynurenic ester from step (c), and stirring the resulting solution until hydrolysis of the ester group thereof is complete, thereby forming a diphenylureido-dihalokynurenic acid sodium salt of Formula VII; and adjusting the pH of the reaction mixture to about 6 with an acid;

(c) filtering the pH adjusted precipitate of step (b), and washing the filter cake comprising sodium salt of Formula VII with water;

(d) adding a sufficient amount of an aqueous carboxylic acid to the filter cake of step (c) to achieve a pH in the range of about 6 to about 7 and stirring the resulting slurry of a diphenylureido-dihalokynurenic acid of Formula VIII until conversion of the sodium salt to the diphenylureido-dihalokynurenic acid is complete;

(e) filtering the slurry from step (d), and washing the filter cake comprising the diphenylureido-dihalokynurenic acid of Formula VIII with water to remove water soluble impurities therefrom;

(f) dissolving the washed filter cake from step (d) in an organic solvent, adding a molar excess of an aqueous solution of p-toluenesulfonic acid thereto, and stirring the resulting slurry of a diphenylureido-dihalokynurenic acid tosylate addition salt of Formula IX until precipitation of the tosylate addition salt is complete; and (g) isolating the diphenylureido-dihalokynurenic acid addition salt of Formula IX;

wherein:

X is halogen;

M is Na, and

R is $C_1$ to $C_4$ alkyl.

In some embodiments of the method for preparing diphenylureido-dihalokynurenic acid addition salts of Formula IX, the sodium hydroxide in step (a) is added while maintaining a temperature below about 5 °C, and then after completing the addition, stirring the mixture at about 20±5 °C until carbamylation of the amino group of the 4-amino-5,7-dihalo-quinoline-2-carboxylic ester is complete.

In some embodiments of the method for preparing diphenylureido-dihalokynurenic acid addition salts of Formula IX, the water is added in step (b) while maintaining a temperature of about 30±5 °C, and the mixture is then stirred at a temperature in the range of about 20 to 45 °C until hydrolysis of the ester group is complete.

The following non-limiting examples are provided to illustrate certain aspects and features of the methods described herein.

EXAMPLES

Experimental Procedure

All the reagents and solvents were purchased from commercial sources and used as received. $^1$H-NMR spectra were obtained using 300 MHz and 500 MHz BRUKER AVANCE 300 or AVANCE 500 spectrometers. Tetramethylsilane from NMR solvents was used as internal reference. HPLC analyses were performed using VARIAN PROSTAR instrument by measuring areas under the peaks (also known as area under curve or AUC) and calculating the percentage of the area under each peak relative to the total area of all peaks (sometimes referred to as area under curve or AUC method).

HPLC Analysis Methods

Column: WATERS XBRIDGE PHENYL, 3.5 μM, 4.6±150 mm

Detector Wavelength: 254 nm;

Flow rate: 1.0 mL/min;

Mobile phase A: 0.05% formic acid in water;

Mobile phase B: 0.05% formic acid in acetonitrile;

Diluent (acetonitrile or acetonitrile with 0.1% TFA for conversion of Formula V to Formulas VI, VII, VIII, and IX.

The elution gradient is found in Table 1.

TABLE 1

HPLC Elution Gradient:

| Time (min) | Flow (mL/min) | % A | % B |
|---|---|---|---|
| 0:00 | 1 | 95 | 5 |
| 5:00 | 1 | 95 | 5 |
| 14:50 | 1 | 10 | 90 |
| 20:36 | 1 | 95 | 5 |
| 25:00 | 1 | 95 | 5 |

Ex. 1. Aza-Michael Reaction to Form Compound 3

3,5-Dichloroaniline 1 (100.0 g, 0.617 mol, 1.0 eq) was charged into a one liter, three-neck, jacketed reactor equipped with mechanical stirrer, reflux condenser and temperature probe, followed by THF (700 mL, 7 vol). Diethyl acetylenedicarboxylate 2 (126.0 g, 0.741 mol, 1.2 eq) was then added into this reactor neat. The addition of diethyl acetylenedicarboxylate was carefully monitored for any exotherm. After the completion of addition, the resulting mixture was stirred at about 70-75 °C during which the reaction was followed by HPLC (about 1 μL of reaction mixture was dissolved in 1.5 mL of MeCN, 5 μL of which was then injected onto the HPLC column). The end point of for the reaction was selected to be at least 75% conversion of 3,5-dichloroanilne (retention time: RT=14.8 min) into Compound 3 (RT=17.5 min), based on HPLC area under curve (AUC) measurements. Upon achieving this conversion, reflux condenser was replaced with distillation head to remove THF under reduced pressure. The end point of THF distillation was determined by $^1$H-NMR. The $^1$H-NMR of the resulting product was consistent with the structure of Compound 3.

Ex. 2. Continuous Flow Synthesis of Compound 3

A. Flow Reactor Design. A fluid pump was connected to a 340 foot coil of ⅛ inch outer diameter (about 3.18 mm), 0.069 inch inner diameter (about 1.75 mm) stainless steel tubing inside of a heating unit. This tubing provided a volume of 3.1 mL for preheating of the reaction mixture and a volume of about 247 mL to provide for suitable residence time for the reaction mixture within the heated coil of the reactor. Using a pump speed of about 4.1 mL/minute, a residence time of about 60 minutes (min) can be achieved. The heater temperature can be set to a desired temperature for the flow reaction. Preferably, a back pressure regulator is tied into the flow line to aid in maintaining a smooth flow rate.

B. Flow Reactor Operation. Since the use of a piston pump with corrosive solvents is not feasible, a peristaltic pump (e.g., a WATSON-MARLOW 530S pump) was used for this reaction, as the resistant tubing within the pump is suitable for use in such corrosive environments. For reactions in neat Eaton's reagent, the substrate Compound 3 was dissolved in Eaton's reagent in a reservoir, while the reactor coil was prefilled with methane sulfonic acid and heated to the desired reaction temperature (e.g., 70 °C.). The reaction mixture was then pumped from the reservoir through the flow reactor coil at a rate sufficient to achieve a desired residence time within the heated coil (e.g., 15 to 40 minutes). Immediately after all of the reaction mixture from the reservoir was pumped into the coil, a chaser of at least one coil volume of methane sulfonic acid was pumped through the coil to ensure that all of the reaction mixture was eluted out of the heated coil. Effluent containing the cyclized product was collected after leaving the heated coil for isolation of Compound 4. A similar process was followed for reactions using a cosolvent with Eaton's reagent, except that the reactor was prefilled with the cosolvent (e.g., DCM) instead of methane sulfonic acid, and the chaser was at least one coil volume of cosolvent, rather than methane sulfonic acid.

C. 54-g Test Reaction with 20 Minute Target Residence Time. The use of a piston pump with corrosive solvents is not feasible. Therefore, a COLE-PARMER L/S peristaltic pump was used in this reaction as the resistant tubing used in this assembly is specifically made for this pump. The reactor was filled with DCM and heated to 70 °C with an internal pressure of 50-70 psi. Compound 3 (54 g) was dissolved in DCM (216 mL, 4 vol) and Eaton's reagent (211 mL, 4 vol) was added. The Compound 3 solution was pumped through the reactor followed by DCM as a chase solvent. After adjusting the pump speed, the residence time was shown to be 23 min using a timer and graduated cylinder. The resulting reaction mixture was collected and HPLC analysis of the reaction mixture indicated 85.5% AUC Compound 4 with 5.8% AUC a byproduct with retention time (RT) of 1.05 min, and 4.2% AUC of Compound 3.

D. 230-g Reaction with 20 Minute Target Residence Time. A WATSON-MARLOW 530S peristaltic pump was used for this flow synthesis to provide a higher flow rate. The reactor was filled with DCM and heated to 70 °C with an internal pressure of 50-70 psi. Compound 3 (230 g) was dissolved in DCM (920 mL, 4 vol) and Eaton's reagent (920 mL, 4 vol) was added. The solution of Compound 3 was pumped through the reactor followed by DCM as a chase solvent. Using a stopwatch, the residence time was shown to be 19.25 min. The resulting reaction mixture was collected and HPLC analysis of the reaction mixture indicated 84.9% AUC Compound 4 with 4.7% AUC of the 1.05 RT byproduct and 0.6% AUC of Compound 3 remaining. During the run, a test of the flow rate indicated only 7 mL/min due to back-flow into the pump. At the completion of the reaction process, it was determined that the average residence time was about 32 min.

E. 10-g Reaction with 20 Minute Target Residence Time. A WATSON-MARLOW 530S pump was used for this flow synthesis. The reactor was filled with methanesulfonic acid and heated to 70 °C with no back-pressure regulator. Crude Compound 3 containing some residual Compound 1 was diluted with Eaton's reagent (40 mL, 4 vol). The solution of Compound 3 was pumped through the reactor followed by methanesulfonic acid as a chase solvent. Using a stopwatch, the residence time was shown to be 16.5 min, less than the target residence time of 20 min. The resulting reaction mixture was collected and HPLC analysis of the reaction mixture indicated 73.7% AUC of Compound 4 with 20.7% AUC of Compound 1.

F. 10-g Reaction with 20 Minute Target Residence Time. A WATSON-MARLOW 530S pump was used for this flow synthesis. The reactor was filled with methanesulfonic acid and heated to 70 °C with a back-pressure regulator set to 15 psi to allow for constant, smooth flow of the output. Crude Compound 3 containing Compound 1 was diluted with Eaton's reagent (40 mL, 4 vol). The Compound 3 solution was pumped through the reactor followed by methanesulfonic acid as a chase solvent. Using a stopwatch, the residence time was shown to be 16 min, less than the target residence time of 20 min. The resulting reaction mixture was collected and HPLC analysis of the reaction mixture indicated 72.7% AUC Compound 3 with 22.3% AUC of Compound 1.

G. Isolation and Purification. The flow reaction mixture (199 g in 1.1 L) was charged at a rate of 40 mL/min into water (2.4 L, 12 volumes) cooled in a jacketed-reactor to −5 °C by keeping the batch temperature below 15 °C. Upon complete addition, the batch was warmed to 23 °C and stirred for additional 0.5 h. Then the batch was filtered to collect the solid. Upon complete deliquoring, the pH of the filtrate was about 0. The filter cake was slurry-washed with 28 wt % solution of NaOAc (2.1 L, 2×5 volumes) to adjust the pH of the cake to about 5 to 6. The filter cake was then washed with water (2.0 L, 2×5 volumes) to remove the inorganic salts. Upon conditioning the cake under vacuum, the cake was transferred into a glass tray to further condition in vacuum oven at 35-40 °C till a constant weight of the cake was reached. The filter cake, mother liquor, and washes were analyzed by HPLC. The crude weight of the filter cake was 197.8 g with 67% purity by HPLC.

Ex. 3. Amination of Compound 4 to Form Compound 5

In a 4-neck, 1 L jacketed-reactor equipped with mechanical stirrer, temperature probe and reflux condenser, was charged Compound 4 (50 g, 1 eq, 0.175 mol) followed by acetonitrile (MeCN; 500 mL, 10 volumes) at 23 °C. The slurry was heated to 70 °C and chlorosulfonyl isocyanate was added slowly (17 mL, 1.1 eq, 0.192 mol,) over 1 h using syringe pump (0.26 min/mL). A controlled evolution of $CO_2$ was observed during the addition of the isocyanate. After complete addition, the mixture was stirred at 70 °C for additional 30 min. Samples were taken before and after chlorosulfonyl isocyanate addition to monitor the consumption of Compound 4 (RT: 14.1 min) to the initial intermediate product (RT: 15-20 min) by HPLC. Upon complete conversion, 1.5 M HCl-EtOH (163 mL, 1.4 eq, 3.2 volumes) was added over 1 h at 70 °C using syringe pump (2.5 mL/min). The addition was followed by HPLC as the disappearance intermediate 15-20 min and appearance of new peak at 11.6 min. The batch was then subjected to vacuum distillation at 50-55 °C. (internal temperature) to reduce the batch volume by about one half. The resulting slurry was then cooled to 0 °C and the pH (1-2) was adjusted using 0.5 N NaOH (165 mL, 1.04 eq. 3.2 volumes) to pH about 9 to 10. The resulting thick slurry was warmed to 5 °C and stirred for addition 0.5 h and filtered to collect the filter cake. Both filter cake and filtrate were analyzed by HPLC. The filter cake, Compound 5, was conditioned in vacuum oven at 45-50 °C overnight. The dry weight of the isolated crude was 46.1 g (crude yield=93%, purity: 90%).

The crude Compound 5 (31 g) was charged into a 4-neck 250 mL jacketed reactor equipped with mechanical stirrer, temperature probe and reflux condenser. EtOAc (155 mL, 5 volumes) was charged into the reactor and the slurry was stirred at 23 °C for 10 min then heated to 50 °C and stirred for 14 h. After 14 h, the mixture was slowly cooled to 23 °C with stirring. The slurry was filtered to collect the filter cake and both filter cake and filtrate were analyzed by HPLC. The filter cake was further conditioned at 40-45 °C for 4 h that provided 25.3 g Compound 4 in 82% yield with 95.8% purity by HPLC.

Ex. 4. Carbamylation to Form Compound 6

Compound 5 (10 g, 0.035 mol, 1 eq) was added into a 4-neck, 500 L jacketed reactor equipped with mechanical stirrer and temperature probe, followed by DMAc (70 mL, 7 vol) and the resulting solution was cooled to 5 °C then diphenylcarbamoyl chloride (9.8 g, 0.042 mol, 1.2 eq) was added as solid in single portion. The solution was stirred for 10 min at 5 °C then NaH (60%, 2.8 g, 0.2462 mol, 2 eq) was added in portions over 1 h at 5 °C. Upon completion of addition, the deep red mixture was stirred for additional 1 h. The progress of reaction was monitored by HPLC. A 10 wt % AcOH solution (280 mL, 4 volumes based on the DMAc volume) was added to another 3-neck 1 L jacketed reactor equipped with mechanical stirrer and temperature probe, and cooled to about 5 °C. The DMAc solution was then slowly pumped into the 10 wt/o AcOH solution to quench the intermediate product and precipitate out crude Compound 6 by keeping the internal temperature around 5 °C. Upon complete quench, the slurry (pH=3) was stirred at 5 °C for an additional 30 min, and then was filtered to collect the filter cake. The filter cake was washed with water (2×140 mL, 2×2 vol) and the filter cake, filtrate, and washes were analyzed by HPLC. The collected filter cake was further conditioned at 45-50 °C for overnight in a vacuum oven to yield 14.6 g (87%) with 87% purity by HPLC.

The crude Compound 6 (42 g) was charged into a 3-neck 1 L jacketed-reactor and DCM (420 mL, 10 volumes) was added to dissolve the material. Upon complete dissolution, 0.5 N NaOH (125 mL, 3 volumes) was added into the reactor and the mixture was vigorously stirred for about 5-10 min and then stirring was stopped to provide a phase separation. Organic phase was collected and charged back into the reactor and the 0.5 N NaOH wash was repeated for 3 times. Upon completion of 0.5 N NaOH washes (3×3 volumes), the organic layer was washed with 0.3 M citric acid (125 mL, 1×3 volume). Both organic and aqueous phases were analyzed after every wash by HPLC, which showed that a 16.7 min impurity was partially purged in base washes, but still remained in organic phase in addition to a 15.9 min impurity.

The organic phase (400 mL) was transferred into a 500 mL reactor equipped with mechanical stirrer, thermocouple, addition funnel and Dean-Stark condenser, and was slowly heated to 45 °C to remove DCM. Upon removal DCM to about 6 volumes EtOH was continuously charged dropwise to maintain 6 volumes of solvent in the still pot, while DCM was distilled away. The temperature of the mixture was slowly raised to 70 °C with constant dropwise addition of EtOH during which crystallization/precipitation was observed. In total, about 250 mL of EtOH (6 volumes) was added, and the mixture was maintained at 70 °C for about 45 min. $^{1}$H-NMR confirmed a 22:1 ratio of EtOH:DCM and a successful swapping of most of DCM to EtOH.

The slurry was slowly cooled over 1 h to 20 °C and maintained at 20 °C overnight with stirring. The slurry was then filtered to collect the solid, and the both filter cake and filtrate were analyzed by HPLC. HPLC data of filter cake confirmed the purging of both 15.9 and 16.7 min RT impurities in EtOH. The filter cake was further conditioned at 50 °C in a vacuum oven for 4 h to provide 27.4 g of purified Compound 6 in 65% yield with over 98% purity by HPLC.

In another preparation, Compound 5 (20.0 g, 0.07 mol, 1 equiv) was dissolved in DMAc (140 mL, 7 vol), and cooled to 5 °C in a four-neck, 1000-L, jacketed reactor equipped with mechanical stirrer and temperature probe. Diphenylcarbamoyl chloride (19.6 g, 0.084 mol, 1.2 eq) was added to the solution of Compound 5 as solid in single portion. The resulting reaction solution was stirred for 15 min at 5 °C then NaH (60%, 5.6 g, 0.52 mol, 2 equiv) was added in portions over 1 h at 5 °C. Upon completion of the addition, the obtained brown mixture was stirred for additional 1 h. The progress of reaction was monitored by HPLC, and was complete after 1 h. In another three-neck, 1-L, jacketed reactor equipped with mechanical stirrer and temperature probe was charged, 10 wt % AcOH solution and cooled to 5 °C. Main reaction mixture was slowly added into 10 wt % AcOH solution (560 mL, 4 vol based on DMAc) at 5 °C to precipitate out crude Compound 6 by keeping the internal temperature around 5 °C. Upon complete quenching of the reaction mixture, the resulting slurry (pH=3) was stirred at 5 °C for additional 30 min then filtered to collect the filter cake. The filter cake was washed with water (2×280 mL, 2×2 vol, based on DMAc) and the filter cake, filtrate, and washes were analyzed by HPLC. The filter cake collected was further conditioned at 45-50 °C for overnight (20 h) in a vacuum oven to yield 33.2 g (98.5%) of Compound 6 with 86% purity.

The crude Compound 6 was split into two parts: part I (16.6 g) was charged into a three-neck, 1-L jacketed-reactor and dissolved in ethyl acetate:methyl ethyl ketone (825 mL, 75:25, 50 vol) at 50 °C. Upon complete dissolution, the solution was cooled to about 22 °C, and 0.5 N NaOH (50 mL, 3 vol) added into the mixture with vigorous stirring for about 5-10 min, after which the stirring was stopped to allow for a phase cut. The organic phase was collected and charged back into the reactor and was washed 3 times with 0.5 N NaOH. The organic layer was then washed with 0.3 M citric acid (50 mL, 1×3 vol). Both organic and aqueous phases were analyzed after every wash by HPLC.

The washed organic phase (700 mL) was transferred into a 1 L reactor jacketed reactor and was slowly heated to 40 °C under vacuum to reduce the amount of ethyl acetate and methyl ethyl ketone to about 6 vol. Ethanol (170 mL, 10 vol) then was added to reactor and mixture was distilled down to 6 vol again. Final mixture was cooled to about 22 °C. The resulting slurry was filtered and washed with ethanol 250 mL (15 vol) and then dried in vacuum oven at 40 °C for 3 days to afford Compound 6 was a white solid. (10.77 g, 64% yield, 91.6% purity).

Ex. 5. Base Hydrolysis to Form Compound 7

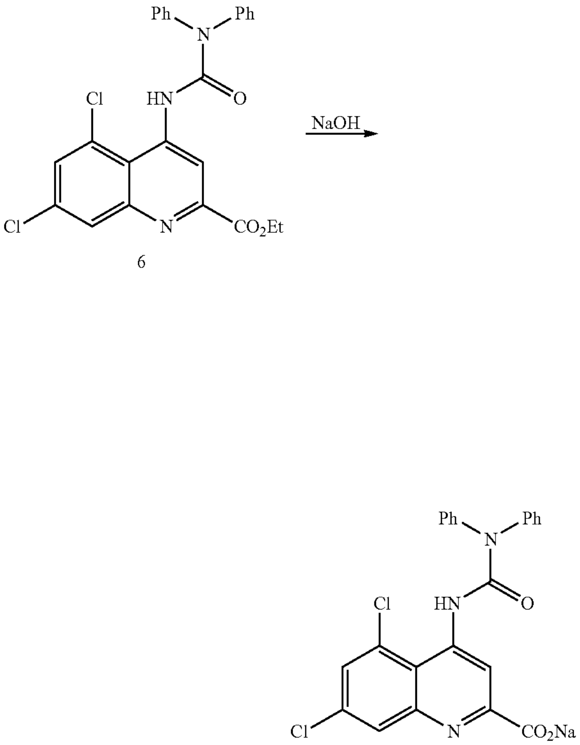

6
7

Compound 6 was hydrolyzed with sodium hydroxide to form the sodium salt, Compound 7. The reaction conditions were demonstrated using GMP lot (run 8, Table 1) on 100 g scale. The reaction proceeded using 2 eq of NaOH and was complete within 3 hours at 50 °C on a 100 g scale (see the 100 g scale run from Table 2. After the hours, the reaction mixture was cooled to room temperature and filtered. The solid was slurried in methanol (2.5 vol) and water (7.5 vol). The pH of the slurry was adjusted to 5 using glacial acetic acid and the mixture was stirred overnight, after which the pH was adjusted again to 5 and the slurry was filtered, washed with methanol (2 vol), and dried in a vacuum oven overnight at 45 °C to afford the desired product in 89% yield (88 g). Different conditions were screened as well, as set forth in Table 2, all of which resulted in high conversions to Compound 7.

TABLE 2

Step 1 Optimization

| Scale | Conditions | Temp/ Time | Isolated Yield (%) | Conversion By HPLC (area %) |
|---|---|---|---|---|
| 10 g | Compound 6 1.0 eq<br>NaOH 50 wt % 3 eq<br>MeOH 5 vol<br>Water 5 vol | 60 °C, 3 h | 10 g<br>102% | 100% |
| 960 mg | Compound 6 1.0 eq<br>NaOH 50 wt % 3 eq<br>Water 10 vol | 80 °C, 24 h | — | 87% |
| 10 g | Compound 6 1.0 eq<br>NaOH 50 wt % 3 eq<br>MeOH 3 vol<br>Water 7 vol | 40 °C, 14 h | — | 100% |
| 10 g | Compound 6 1.0 eq<br>NaOH 50 wt % 3 eq<br>MeOH 10 vol<br>Water 10 vol | 40 °C, 14 h | 10.6 g<br>106% | 100% |
| 10 g | Compound 6 1.0 eq<br>NaOH 50 wt % 2 eq<br>MeOH 10 vol<br>Water 10 vol | 50 °C, 2 h | 10.1 g<br>102% | 100% |
| 20 g | Compound 6 1.0 eq<br>NaOH 50 wt % 2 eq<br>MeOH 7.5 vol<br>Water 7.5 vol | 50 °C, 2 h | 21 g<br>105% | 100% |
| 250 g | Compound 6 1.0 eq<br>NaOH 50 wt % 2 eq<br>MeOH 7.5 vol<br>Water 7.5 vol | 50 °C, 3 h | 220 g<br>89% | 100% |
| 100 g | Compound 6 1.0 eq<br>NaOH 50 wt % 2 eq<br>MeOH 7.5 vol<br>Water 7.5 vol | 50 °C, 3 h | 88 g<br>89% | 100% |

Ex. 6. Formation of Tosylate Addition Salt, Compound 8

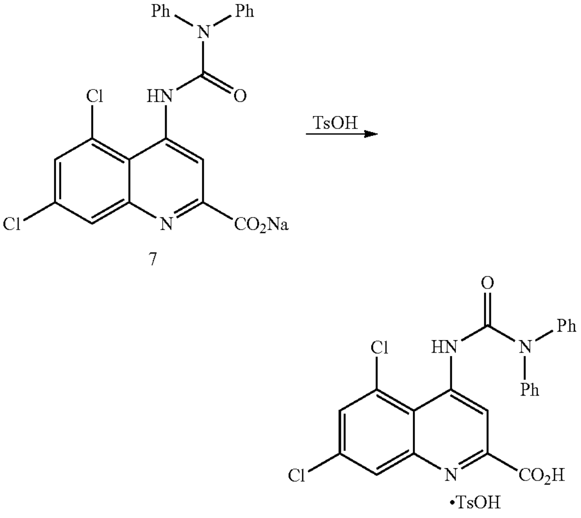

7
8

Formation of Compound 8 was achieved by addition of about 2 equivalents of p-toluenesulfonic acid to Compound 7. Various reaction conditions were examined, as shown in Table 3. A 200 g scale run (Table 3) is provided as an illustration of the process. The dried Compound 7 material was slurried in ethyl acetate (1.2 L, 6 vol) and warmed to about 40 °C. A 2.1 M aqueous solution of p-toluenesulfonic acid (prepared from 160 g of p-toluenesulfonic acid monohydrate dissolved in 240 mL of water) was added to the ethyl acetate slurry, which was then stirred at 40 °C for 10 hours and then was cooled to 10 °C over 1 hour. Proton NMR at this point showed about 80% conversion to the desired salt. The slurry was then rewarmed to 40 °C and was treated with an additional portion of 2.1 M p-TsOH solution (100 mL, 40 g of p-toluenesulfonic acid in 60 mL of water) and was stirred at 40 °C for 2 hours, after which proton NMR showed complete conversion to the tosylate addition salt. The slurry then was cooled to 10 °C over 1 hour, aged for 1 hour at 10 °C, and was filtered. The filter cake was washed with ethyl acetate (2-400 mL, 2×2 vol) and dried at 45 °C to afford 220 g of the desired product in 84% yield.

TABLE 3

Addition Salt Formation

| Scale | Conditions | Temp/Time | Isolated Yield (%) | Conversion By HPLC (area %) |
|---|---|---|---|---|
| 10 g | Compound 7 1.0 eq<br>TsOH • $H_2O$ 1 eq<br>EtOAc 6 vol<br>Water 0.7 vol | 60 °C, 3 h | 6.5 g<br>49% | 10% |
| 10 g | Compound 7 1.0 eq<br>TsOH • $H_2O$ 2 eq<br>EtOAc 6 vol<br>Water 0.7 vol | 60 °C, 3 h | 6.5 g<br>49% | 100% |
| 10 g | Compound 7 1.0 eq<br>TsOH • $H_2O$ 2 eq<br>EtOAc 6 vol<br>Water 0.7 vol | 45 °C, 14 h | 13.0 g<br>100% | 100% |
| 3 g | Compound 7 1.0 eq<br>TsOH • $H_2O$ 2 eq<br>EtOAc 6 vol<br>Water 1.7 vol | 45 °C, 14 h | — | 80% |
| 10 g | Compound 7 1.0 eq<br>TsOH • $H_2O$ 2 eq<br>EtOAc 6 vol<br>Water 0.7 vol | 40 °C, 14 h | 7.0 g<br>70% | 100% |
| 200 g | Compound 7 1.0 eq<br>TsOH • $H_2O$ 2 eq<br>EtOAc 6 vol<br>Water 1.2 vol | 40 °C, 14 h | 220 g<br>84% | 100% |

Ex. 7. Direct Synthesis of Tosylate Addition Salt, Compound 8, from Compound 5

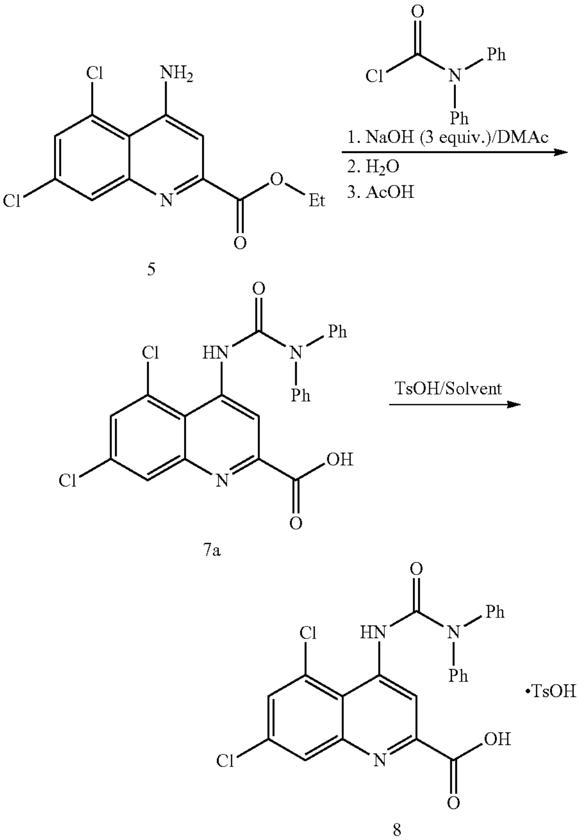

5, 7a, 8

Direct conversion of amine 5 to tosylate addition salt 8 was performed as follows: A 5 L jacketed reactor equipped with an over headed stirrer, $N_2$ gas inlet and a thermocouple was purged with nitrogen. To the reactor was added amine 5 (230 g, 806.68 mmol, 1 eq.), diphenylcarbamoyl chloride (230 g, 992.21 mmol, 1.23 eq. Acros Organics, Lot #A0408840) followed by DMAc (1.38 L, 6 vol, Sigma Aldrich, Lot #SHBN8219, KF=433 ppm) and the resulting solution was stirred at <5 °C for about 10 min, and then NaOH (powder, 96.80 g, 2420.03 mmol, 3 equiv, Aldrich, Lot #757527-PW) was charged in ten portions over 2 h at below 5 °C. After completion of the NaOH charge, the deep red mixture was stirred for 3 h at ambient temperature. The progress of the carbamylation reaction was monitored by HPLC. In Process Control (IPC) of the reaction mixture showed ≤2% conversion of the staring material 5. The reaction mixture was then agitated at 20±5 °C for 18 h (overnight). Next, deionized (DI) water (2.76 L, 12 vol.) was charged slowly into the reaction mixture while maintaining batch temperature at about 30±5 °C. The initially bright red solution was turned into a yellow thick slurry of ethyl ester 6. Additional DI-water (460 mL, 2 vol.) was charged. The batch was agitated for 18 h at 30±5 °C. The IPC of the reaction mixture then showed ≤1% conversion of the ethyl ester 6 to the sodium salt 7. After stirring overnight, the pH was adjusted pH=6.5±0.5 by adding acetic acid (AcOH) (155 mL, Sigma Aldrich, Lot #MKCK9445) at room temperature. The pH of the mixture was checked by pH paper, and then the reaction mixture was filtered using glass sintered funnel (3 L, medium, diameter 5.5 inch). After filtration, the filter cake was rinsed with DI-water (690 mL, 3 vol.).

The wet cake was then charged back to the 5 L jacketed reactor. $AcOH/H_2O$ mixture (3:7, 5 vol, 345 mL AcOH, 805 mL $H_2O$) was prepared in a separate carboy. Then the $AcOH/H_2O$ mixture was charged to the reactor and the batch was agitated at ambient temperature for about two days. The mixture was then cooled down to 10±5 °C and agitated at this temperature for 1 h. The reaction mixture slurry was then filtered using a glass sintered funnel (2 L, medium, diameter 5.5 inch) and rinsed with water (920 mL, 4 vol.) two times to remove excess sodium acetate to afford carboxylic acid 7a. The filter cake of carboxylic acid 7a was charged back to the same reactor followed by ethyl acetate (1.82 L, 5 vol., bulk). The resulting solution was agitated for about 15 minutes at 20±5 °C.

In a separate carboy 3M p-toluenesulfonic acid monohydrate (PTSA) solution (184.14 g $p\text{-}TsOH\cdot H_2O$, 968.01 mmol in 138.5 mL DI-water, Sigma Aldrich, Lot #MKCQO139) was prepared. The PTSA solution (322.67 mL) was added to the solution of 7a at 20±5 °C over 30 minutes. The reaction mixture initially became biphasic; however, within an hour the yellowish green solid TsOH addition salt 8 started to precipitate out. The batch was agitated for 18 h at 20±5 °C. The reaction progress was checked by proton NMR and showed complete conversion into the desired addition salt 8. The mixture was then cooled down to 10±5 °C and agitated at this temperature for 3 h. Next, the mixture was filtered using a glass sintered funnel (2 L, medium, diameter 5.5 inch). The filter cake was rinsed with ethyl acetate (230 mL, 1 vol.) and dried in a vacuum oven at 40±5 °C, and afterward 354.9 g of the desired greenish yellow solid addition salt 8 was isolated (354.9 g, 70.5% isolated yield starting from amine 5, water content=8372 ppm (0.8 wt %) by Karl Fischer analysis, AcOH content=0.3 wt % from proton NMR, HPLC purity: 99.71% by HPLC AUC.

In comparison, 230 g of Compound 5 yielded 257.3 g of addition salt 8 using NaH as the base and isolating the various intermediates, such as carbamylated ester 6 and sodium salt 7, whereas with the direct process provided 354.9 g of addition salt 8 isolated), and with excellent purity (99.71% by HPLC AUC).

Preferred embodiments of this invention are described herein, including the best mode known to the inventors for carrying out the invention. Variations of those preferred embodiments may become apparent to those of ordinary skill in the art upon reading the foregoing description. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A crystalline compound having a formula of:

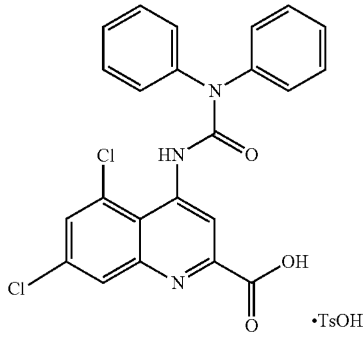 [SMILES: O=C(O)c1cc(NC(=O)N(c2ccccc2)c2ccccc2)c2c(Cl)cc(Cl)cc2n1]

•TsOH, wherein the TsOH is p-toluenesulfonic acid.

2. The crystalline compound of claim 1, wherein the crystalline compound has a purity of greater than 98%.

3. The crystalline compound of claim 1, wherein the crystalline compound is an addition salt derived from p-toluenesulfonic acid and a compound having a formula of:

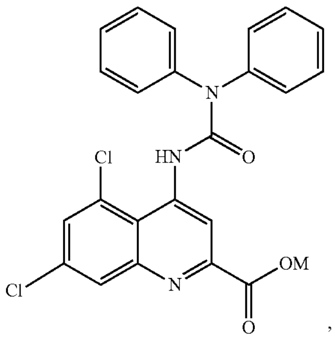

, where M is a cation.

4. The crystalline compound of claim 3, wherein the cation is sodium ($Na^+$).

5. The crystalline compound of claim 1, wherein the crystalline compound is comprised in a composition.

6. The crystalline compound of claim 5, wherein the composition comprises water.

7. The crystalline compound of claim 6, wherein the composition further comprises ethyl acetate.

8. The crystalline compound of claim 1, wherein the crystalline compound is an analgesic agent.

9. A method of treating a subject identified as having chronic pain, the method comprising administering to the subject the crystalline compound of claim 1, wherein the chronic pain of the subject is treated.

* * * * *